United States Patent [19]

Ewing

[11] 4,443,479

[45] Apr. 17, 1984

[54] PHARMACEUTICAL METHODS AND COMPOSITIONS USING PARABENZOQUINONE

[76] Inventor: Channing B. Ewing, P.O. Box 47, East Lake Weir, Fla. 32632

[21] Appl. No.: 466,141

[22] Filed: Feb. 14, 1983

Related U.S. Application Data

[62] Division of Ser. No. 370,066, Apr. 20, 1982, Pat. No. 4,382,095.

[51] Int. Cl.$^3$ .............................................. A61K 31/12
[52] U.S. Cl. ................................................... 424/331
[58] Field of Search ........................................ 424/331

[56] References Cited

U.S. PATENT DOCUMENTS 2,937,919 5/1960 Pasternols ............................ 424/331

OTHER PUBLICATIONS

Chem. Abs. 90, (1979)-17218H, 95, (1981), 181081G.

*Primary Examiner*—Stanley J. Friedman
*Attorney, Agent, or Firm*—Cushman, Darby & Cushman

[57] ABSTRACT

Bronchial asthma including bronchial spasms associated therewith are treated with pharmaceutical compositions containing small amounts of parabenzoquinone, for instance 2 milliliters of a one part per million solution of PBQ in sterile isotonic saline solution. This solution is administered to an asthma patient. Typically the same dose is repeated again in a month or so and the asthma symptoms are alleviated.

2 Claims, No Drawings

PHARMACEUTICAL METHODS AND COMPOSITIONS USING PARABENZOQUINONE

This is a division of application Ser. No. 370,066, filed Apr. 20, 1982 now U.S. Pat. No. 4,382,095.

BACKGROUND OF THE INVENTION

This application relates to methods of treating various disease states and more specifically to a method of administering pharmaceutical compositions containing highly diluted amounts of parabenzoquinone to a subject in need of such therapy.

Parabenzoquinone, or as it is known chemically 1,4-benzoquinone, quinone or chinone, has the formula $C_6H_4O_2$, is a known staple of commerce used in the manufacture of dyes, hydroquinone, fungicides, as an analytical reagent, in photography, and as an oxidizing agent. It appears in the form of yellow crystals and has a rather irritating odor. It is soluble in alchol, ether and alkaline solutions but only slightly soluble in hot water. It has a specific gravity of 1.307 and a melting point of 115.7° C. Parabenzoquinone, or PBQ as it is sometimes referred to hereinafter, is reported to be toxic when inhaled and a strong irritant to the skin and mucus membrane, with a tolerance value of 0.1 parts per milion (ppm) in air; see the Condensed Chemical Dictionary, 10th Edition, Halley, editor (1981) page 879, and also Dangerous Properties Of Industrial Materials, by Sachs, editor, 4th Edition (1975) pp. 1074-1075 which describes quinone as causing severe local damage to skin and mucus membranes by contact with it in the solid state, in solutions or the form of condensed vapors. The art has accepted a criterion for regulating work room concentration of quinone in the air according to personal comfort of the individuals involved as judged by eye irritation. The oral $LD_{50}$ in rats is reported to be 130 mg/km.

BRIEF DESCRIPTION OF THE INVENTION

Despite these severe warnings I have surprisingly found, however, that very dilute solutions of parabenzoquinone—of the order of 1 part per million (ppm)—may be used either by injection or in the form of an oral composition, for instance a tablet, for the treatment of various disease states including both the central nervous system and the para-sympathetic portion of the autonomic nervous system. Further, I have found that when sterile water is used as the vehicle for diluting the PBQ upon injection severe pain and discomfort results in the subject, but that when isotonic saline in used as the diluent the pain on injection is significantly and substantially reduced to a manageable level.

DETAILED DESCRIPTION OF THE INVENTION

According to my invention, methods and procedures are described for the treatment of various disease states in which a small amount of a dilute composition containing parabenzoquinone is administered to a subject in need of same to alleviate or remove the symptoms caused by a particular condition or disease state. More specifically, according to my invention parabenzoquinone, in a concentration of about 1 ppm, is administered in small quantities to individuals suffering from various conditions. The amount of PBQ administered per dose may vary depending upon the symptoms being treated and the size and condition of the patient. Generally each dosage will be in the range of 1 to 1 million micrograms (mcg), and preferably 1-2 mcg. My invention also includes pharmaceutical compositions containing an amount of parabenzoquinone sufficient to treat the particular condition or disease state for which it is administered typically 1 or 2 mcg for each ml of solution when parenteral pharmaceutical compositions are contemplated.

In general, the administration of PBQ corrects most aberrations occurring in the nervous system, both in the central nervous system and in the para-sympathetic portion of the autonomic nervous system. PBQ administration in appropriate quantities, in my view, serves to re-establish the normal oxidative mechanism that is present in the body at all times thus restoring nervous function to a more ready normal rate.

Illustrative of the conditions treated by the procedures of my invention one may mention depressive psychosis; spasms occasioned by bronchial asthma; chronic central nervous system (CNS) disorders, particularly grand mal epilepsy for the tonic-clonic seizures. The compositions are also used to treat and stabilize the autonomic nervous system, in the treatment of herpes zoster, as a nonspecific antibiotic, in the treatment of essential hypertension, treating the symptoms of thrombo pheblitis and in cases of nervous fatigue and collapse. The therapy is also useful in treating smooth muscle spasms and also muscle spasms that are associated with peptic ulcers. I have found the treatment to be additionally useful in alleviating the withdrawal symptoms caused by overuse of tranquilizers andd/or alcohol. Also migrane headaches are successfully treated by this therapy.

According to the procedure of my invention, a pharmaceutical composition containing 1 part per million of parabenzoquinone is adminstered to a subject suffering from one or more of the above-listed conditions. The treatment is continued periodically as may be required until the symptoms of the condition are substantially eliminated or completely eliminated. The preferred route of administration is via injection and specifically an intra-muscular (I.M.) injection of 2 mls of an isotonic saline solution containing 1 part per million parabenzoquinone, that is 2 mcg for each 2 ml of solution. Oral forms of therapy are also within the scope of the present invention and they include tablets, capsules, syrups, elixirs and troches containing the requisite amount of parabenzoquinone.

It will be understood that where a disorder of a kind calling for treatment in animals arises, the present invention while described primarily in terms of human medicine and treatment is equally applicable to the veterinary field.

Pharmaceutical presentation—the compositions according to my invention are conveniently in a form suitable for oral, rectal, parenteral or topical administration in a suitable pharmaceutical vehicle. Tablets may be prepared by mixing a 1 ppm PBQ solution with the required amount of lactose then the lactose/PBQ is compressed into coherent shapes of the appropriate size. A typical dosage form is 0.5 mcg PBQ in a 5-grain lactose tablet or pill, although 2 mcg may be included in a single 5-grain tablet if desired. To facilitate the manufacturing operation before compression the powders may advantageously be mixed also with binders and/or lubricants, such as starch, pectin, gelatin, gum arabic, methylcellulose, carboxyl-methyl cellulose (preferably in the form of its sodium salt), talc, stearic acid and magnesium stearate. The coherent tablets thus formed may be coated, for example with sugar to improve their appearance, taste and durability, and may, moreover, be scored to facilitate administration of smaller doses, if desired.

Capsules may be prepared by enclosing PBQ and a suitable diluent, for example, lactose, within a casing or sheath formed of gelatin, glycogelatin or another suitable material. The nature of this material is chosen in relation to the point in the digestive system at which it is desired to release the active material. It is conveniently either of melting point less than body temperature, or soluble in gastric juices, thus, for example, at PH's of 2 or less, or 9 or more.

Syrups and elixers may be prepared by dissolving or suspending the active material (PBQ) in aqueous liquid media, which may contain a sweetening agent such as sugar, saccharin or a polyhydric alcohol like glycerol or sorbitol, or another flavoring agent, such as alcohol, chloroform, citrates, or of course both. In the case of suspensions, surface-active agents such as glyceryl monostearate, aluminium monostearate and/or ethyl oleate may be incorporated to maintain the suspension, and solubilizing agents may be employed in solutions, together with suitable cosolvents such as alcohols, chloroform and trichloroethylene, if these are not already present. The thixotropy and viscosity of the liquid medium may be adjusted by the inclusion of appropriate amounts of pecitn, gelatin, gum tragacanth, carboxymethyl-cellulose, or agar-agar. Colorants may also be incorporated.

Injectable preparations may be prepared by forming solutions and/or suspensions in any of the usual sterile media, which may be oily but is preferably aqueous. Preferably the preparations are rendered isotonic with the body fluids and adjusted to the desired viscosity.

It will be understood that the absolute quantity of active ingredients present in any dosage unit should not exceed that appropriate to the rate and manner of administration to be employed, but on the other hand should also desirably be adequate to allow the desired rate of administration to be achieved by a small number of doses. The rate of administration will moreover depend on the precise pharmacological action desired.

While the mechanism of action of parabenzoquinone in the procedure of my invention is not known to a certainty, and while I do not wish to be bound or limited to any particular theory, it would appear that many diseases, including the functional disturbances of the nervous system, are due to a chemical imbalance in that system, typically insufficient metabolic oxygen leaving the patient with a metabolic hypoxie. Parabenzoquinone is considered to be a highly sufficient oxygen catalyst which may be responsible for the therapeutic properties of this material.

The carbonyl present in PBQ: The conjugated systems of carbonyl and ethylene linkages occurring in parabenzoquinone are used to initiate a chain reaction by autooxidation in the ethylene linkages. The double bonds present are thought to give this greater power in initiating the oxidative catalyst process and maintaining it for long periods of time. The oxidative process, once initiated, proceeds as a chain reaction, growing in intensity in geometric proportions. This process not only removes all of the hydrogen ions from the above-mentioned metabolic residue, but also restores the oxidative metabolic process to a more nearly normal state. This represents the end result of metabolic detoxication, thus eliminating the false nerve stimulation to the nervous system.

My invention will now further be illustrated by the following examples in which all parts and percentages are by weight, unless otherwise indicated.

EXAMPLES OF THE INVENTION

Example 1

Treatment of Asthma: a patient, male, 58 years of age who had suffered previously for 10 years with asthma, was examined and diagnosed as having bronchial asthma influenced and maintained by a high degree of allergic rhinitis. The patient was administered 2 ml of a 1 part per million (ppm) solution of parabenzoquinone (2 mcg PBQ per dose) intra-muscularly and gradually the patient's asthma attacks became remarkably improved. After three months, the patient had gained 10 pounds in weight. Three months later, the treatment was repeated and one month treated after the patient was improved to the extent that the symptoms of asthma and hay fever were no longer a physical problem to him.

Example 2

A male, 57 years of age, was diagnosed as having chronic bronchial asthma with bronchieactasis. Two mls. of a 1 ppm solution of PBQ were administered I.M. and examined 30 days thereafter. The patient reported that spasms of the asthma had receded to the point where the patient could lie flat in bed and sleep through the night, a condition that had not been possible for the past several years. Three months after the initial treatment, the general health of the patient was improved and he had gained several pounds. The treatment (2 mls. of a 1 ppm PBQ solution I.M.) was repeated three months after the second examination and 6 months after the initial treatment improvement continued with the final absence of bronchial spasms. The bronchieactasis was somewhat improved at the end of treatment perhaps due to postural exercises.

Example 3

The son, age 9, of the patient of Example 2 was examined and diagnosed to have chronic bronchial asthma with allergic rhinitis. A solution of 2 ml of 1 ppm PBQ was administered I.M. and 30 days thereafter an improvement was shown in the asthmatic spasms which would then occur only at the height of an allergic attack. The treatment was repeated after 30 days from the initial treatment and the patient remained free of asthma symptoms. Additionally, hay fever was no longer a problem.

Example 4

A woman, age 16, complained of symptoms of claustrophobia, the fear of eating in public places and generally in a constant state of deep anxiety. Periodically there would be sessions of deep depression and a general fear of crowds. The patient was diagnosed as suffering from severe nervous fatigue and anxiety neurosis. Two mls. of a sterile isotonic solution of 1 ppm of PBQ were administered I.M. and administration was continued every two months for a total of three doses. At the conclusion of therapy the depressed state and the level of anxiety began to subside and the patient resumed normal employment functions.

Example 5

A male patient, age 67, complaining of hypertension and a general state of neurosis which had existed for at least three years and increasing with time was examined. He was also found to have extensive tremors with both hands. Partial relief of his symptoms was obtained by the administration of two 5-grain tablets each containing 0.33 microgram of PBA. This improvement in the patient's condition was noticed within two hours of administering the tablets.

Example 6

A male, age 64, was diagnosed as having hypertension and was observed to lack a certain degree of emotional stability. He was treated with six tablets each containing 0.33 microgram of PBQ and within three days the emotional stability had returned and within one week his blood pressure had returned to normal. No further medication was given the patient and after a period of one year he was reexamined and found to be normal and free of the symptoms of which he was previously complaining.

Example 7

A female, age 60, who complained of migrane headaches and was generally irritable. Four tablets, each containing 0.33 microgram of PBQ, were given her. The patient was observed and steady improvement in her condition was noted in that the migrane headaches occurred with much less frequency and when they did occur they were less severe and lasted for a shorter duration than prior to treatment.

Example 8

A male, age 34, was diagnosed as suffering from anxiety neurosis with recurrent symptoms of a peptic ulcer. He complained of pain when his stomach was empty and was unable to sleep well. He was given 0.33 mcg. of PBQ in tablet form administered as a single dose. After three days, the patient reported that his sleeping pattern had changed to one of complete rest and the anxiety was being relieved in a gradual manner. After one week, the patient reported that all distress and discomfort about his stomach had disappeared and a follow-up one year later indicated that all the symptoms previously observed had dissipated.

Example 9

A male, age 58, complained of migrane headaches that occurred in approximately two-week intervals. The headaches were described as being very severe; the patient reported that these headaches occurred periodically over the past four years. The headaches would persist for at least four days at a time. The patient was given four tablets each containing 0.33 mcg. of PBQ. A year later, without any further treatment, the patient was checked and reported that he was free from any symptoms of migrane headaches. The therapy was repeated one year after initial treatment as a prophylactic measure.

Example 10

A male, age 32 years of age, complained of chronic and persistent headaches in the region of the frontal sinus and was tentatively diagnosed as suffering from sinusitis. He was given four tablets each containing 0.33 mcg. of PBQ in a single dose. Two days later he was free of the headaches and has remained so.

Example 11

A female patient, age 56, complained of severe and persistent depression sometimes extending for periods of months. She was treated for an ulcerated stomach as well. She was diagnosed as having a peptic ulcer with anxiety neurosis and was given four tablets each containing 0.33 mcg. of PBQ administered in a single dose. One week after administration the patient reported that she was sleeping well and improving. Her peptic ulcer symptoms had disappeared ten days following administration and she was able to eat her choice of foods without digestive flare-ups.

Therapy was continued by giving the patient 0.66 mcg. every six months to control the nervous fatigue and neurosis. During the course of therapy, one of the six month intervals was inadvertently extended to eight months and at the time she reported that the symptoms of depression began to recur. However, shortly after taking the prescribed amount of PBQ the symptoms of depression were alleviated.

Example 12

A male, age 60, suffering from violent nervous tremors had been taking excessive quantities of tranquilizers of an amount and identity unknown, and was given an injection of 2 ml of an isotonic sterile solution (1 ppm) of PBQ. In 24 hours, the patient was examined and found to be virtually free of the violent tremors. He reported that his sleep was undisturbed and that his previous interest in tranquilizers had completely subsided. A second dose of 2 ml ml of a 1 ppm solution adminstered four days after the first dose and within one week of the first dose he returned to his work. The patient was followed and six months after the initial treatment was again given a 2 ml injection of 1 ppm PBQ.

EXAMPLE 13

Treatment of senile dementia—a male, age 84, suffering from severe senile dementia for four months and exhibiting an elevated blood pressure was examined. The patient had been given various tranquilizers and depressants in order to make him more manageable, but without positive results. Tranquilizer therapy was discontinued and the patient was given 2 mcg. of PBQ orally. A change in personality was noted within a few hours after therapy and that night the patients's 79 year old wife reported the couple successfully resumed marital relations after an approximate 20 year period of inactivity.

The patient was given an additional 2 mcg. of PBQ four months after the initial therapy and had started playing golf without symptoms of his previous anti-social behavior.

Based upon my experience and observations as illustrated by the above clinical examples, it is suggested that patients susceptible to the treatment according to my procedure generally divide themselves into two categories. In many instances the first injection or administration of the drug is sufficient to initiate the process of recovery of an apparent biochemical insufficiency in the patient. Within three days if it is evident to both the patient and the physician that no recovery process has been instituted, the dosage should be repeated at once. Again, after a period of about 30 days or so from the second dosage the patient should be examined to determine the extent of the recovery process.

I have found that the procedures according to my invention are highly effective in the treatment of persons suffering from asthma and the bronchial spasms associated therewith. It is also to be noted that this therapy is compatible with antihistamines and in fact it is recommended that antihistamine therapy be used concurrently with the procedures according to my invention. Suitable histamine antagonists (antihistamines) are known in the art; see Goodman and Gilman, "The Pharmacological Basis of Therapeutics", 5th Edition (1975), pp. 603–629, particularly Table 29-2, the disclosure of which is incorporated herein by reference.

The procedures of administering the pharmaceutical compositions described herein require a certain degree of care and planning. If an injectable form is used, care must be taken in the sterilization and cleaning not only of the patient's skin but also of the instruments used. For instance, the skin should be wiped dry of any traces of alcohol used for disinfecting purposes. Also, it is recommended that the equipment used to administer the drug parenterally, namely the syringe and the needle, be sterilized by autoclave rather than chemically. Preferably a single use or "disposable" syringe is used having a 26 gauge ½ inch needle.

What is claimed is:

1. A method for treating the symptoms of:
   migrane headaches,
   peptic ulcer,
   sinus headaches,
   senile dementia,
   comprising administering to a person suffering therefrom an effective amount of parabenzoquinone and continuing said administration, as required, until the symptoms have been alleviated.

2. The method of claim 1, wherein a pharmaceutical composition containing about 2 parts per million PBQ contained in a compatible, pharmaceutically-acceptable vehicle is administered to said patient.

* * * * *